(12) United States Patent
Mengel et al.

(10) Patent No.: US 7,408,158 B2
(45) Date of Patent: Aug. 5, 2008

(54) GAS SENSOR APPARATUS

(76) Inventors: Arthur H. Mengel, 2 Riga La., Birdsboro, PA (US) 19508; Otto J. Gregory, 2 Riga La., Birdsboro, PA (US) 19508; M. Bradley Feick, 2 Riga La., Birdsboro, PA (US) 19508; David R. Flanders, 2 Riga La., Birdsboro, PA (US) 19508

(*) Notice: Subject to any disclaimer, the term of this patent is extended or adjusted under 35 U.S.C. 154(b) by 157 days.

(21) Appl. No.: 11/441,426

(22) Filed: May 26, 2006

(65) Prior Publication Data

US 2007/0272866 A1 Nov. 29, 2007

(51) Int. Cl.
*G01N 21/35* (2006.01)
(52) U.S. Cl. .................................. 250/338.2

(58) Field of Classification Search ............... 250/338.2
See application file for complete search history.

(56) References Cited

U.S. PATENT DOCUMENTS

| 4,708,989 A | * | 11/1987 | Broussoux et al. | 525/199 |
| 5,105,084 A | * | 4/1992 | Nagai et al. | 250/338.3 |
| 5,341,214 A | * | 8/1994 | Wong | 356/437 |
| 5,418,365 A | * | 5/1995 | Robin et al. | 250/338.2 |

* cited by examiner

*Primary Examiner*—Constantine Hannaher
(74) *Attorney, Agent, or Firm*—Zachary T. Wobensmith, III

(57) ABSTRACT

A gas sensor apparatus for detecting the presence of selected or target gases which has a Quantum Ferroelectric Copolymer sensing element, which is bombarded with infrared radiation and in the presence of a target gas provides an electrical output dependent upon the infrared absorption band of the target gas.

9 Claims, 5 Drawing Sheets

GAS SENSOR APPARATUS

BACKGROUND OF THE INVENTION

1. Field of the Invention

This invention relates to a sensor apparatus for detecting the presence of selected or target gases where a Quantum Ferroelectric (QFE) copolymer sensing element in a housing is bombarded with infrared energy, which element includes a selected QFE copolymer that provides an electrical output dependent upon the IR absorption bands of the gases to be detected.

2. Description of the Prior Art

In the past, before the advent of passive type gas detectors, industrial safety and processing applications made use of robust and expensive electrochemical reactive type systems. The production of economical home safety sensors and commercial air handling apparatus for ventilation control has come to fruition due to the development of semiconductor and infrared sensitive ferroelectrics such as TriGlycine Sulfide and other crystalline materials. These materials are used as a component of the sensing element in apparatus which includes an outer can, a top mounted infrared filter to allow infrared energy only to pass through, and a sensing element, which contains materials that produce an electrical output when bombarded with infrared energy. This output is used to signal the presence of gas in the apparatus between the infrared source and the sensing element.

Crystalline ferroelectrics have become an industry standard sensor for use in Carbon Monoxide and Carbon Dioxide gas detection systems. Due to the hydroscopic nature of these crystalline sensing elements they are difficult to calibrate for the long term, have a short shelf life, with relative instability being the prime factor for potential liabilities, necessitating increased stocking and maintenance costs.

Some specific problems associated with a TGS Pyroelectric Detector are: Maximum operating temperature of 40° C. Responsivity progressively decreases at temperatures below 32° C., which is the optimum temperature (i.e., curie point of TGS). Maximum resolvable temperature differential of about 5° C. The need to repole the TGS crystal when its low Curie temperature is exceeded. TGS is hydroscopic and mechanically fragile. The operating lifetime of the TGS sensor crystal is about 2000 hours as a result of out gassing of the crystal, after prolonged exposure to infrared radiation.

The invention uses quantum ferroelectric copolymers (QFE) in place of the TriGlycine Sulfide (TGS) sensing element in traditionally accepted industry standard, non dispersing infrared (NDIR) gas sensors. Systems utilizing TGS as the sensing element are performance limited by the hydroscopic nature of the crystalline material. Atmospheric moisture, in gas form or condensation as encountered in commercial air handling systems, has a severe detrimental effect on the sensitivity and usable life cycle of the TGS infrared detector. QFE as a replacement for TGS as an NDIR sensing material operating at room temperature in the Pyroelectric mode, does not suffer from the prior art problems, and provides many advantages.

SUMMARY OF THE INVENTION

Detector apparatus for detecting the presence of selected or target gases, which includes a housing containing a sensing element which includes a quantum ferroelectric copolymer material, which housing is in a chamber into which target gases flow, and which chamber contains a source of infrared radiation, which bombards the sensing element with infrared radiation, with the copolymer exhibiting a measurable photo voltaic and current response, when irradiated at radiation bands where the gases to be detected have characteristic infrared radiation absorption bands, which determine the infrared frequencies which reach the sensing element and cause a response by the copolymer material.

The principal object of the invention is to provide a gas sensor apparatus, which includes a housing containing a sensor element with a Quantum Ferroelectric Copolymer coating, which is bombarded by infrared radiation causing the copolymer to respond with a measurable photovoltaic response in the presence of selected gases.

A further object of the invention is to provide an apparatus that can be used to detect a variety of gases by varying the copolymer composition.

A further object of the invention is to provide an apparatus that has a high degree of accuracy.

A further object of the invention is to provide an apparatus that is simple to construct, but sturdy and reliable in use.

A further object of the invention is to provide an apparatus that can use a variety of single copolymers and blends thereof in its gas-sensing element.

Other objects and advantageous features of the invention will be apparent from the description and claims.

DESCRIPTION OF THE DRAWINGS

The nature and characteristic features of the invention will be more readily understood from the following description taken in connection with the accompanying drawings forming part hereof in which.

It should, of course, be understood that the description and drawings herein are merely illustrative, and that various modifications and changes can be made in the structures, and embodiments disclosed without departing from the spirit of the invention.

DESCRIPTION OF THE PREFERRED EMBODIMENT

When referring to the preferred embodiment, certain terminology will be utilized for the sake of clarity. Use of such terminology is intended to encompass not only the described embodiment, but also technical equivalents, which operate and function in substantially the same way to bring about the same result.

Figure 1:
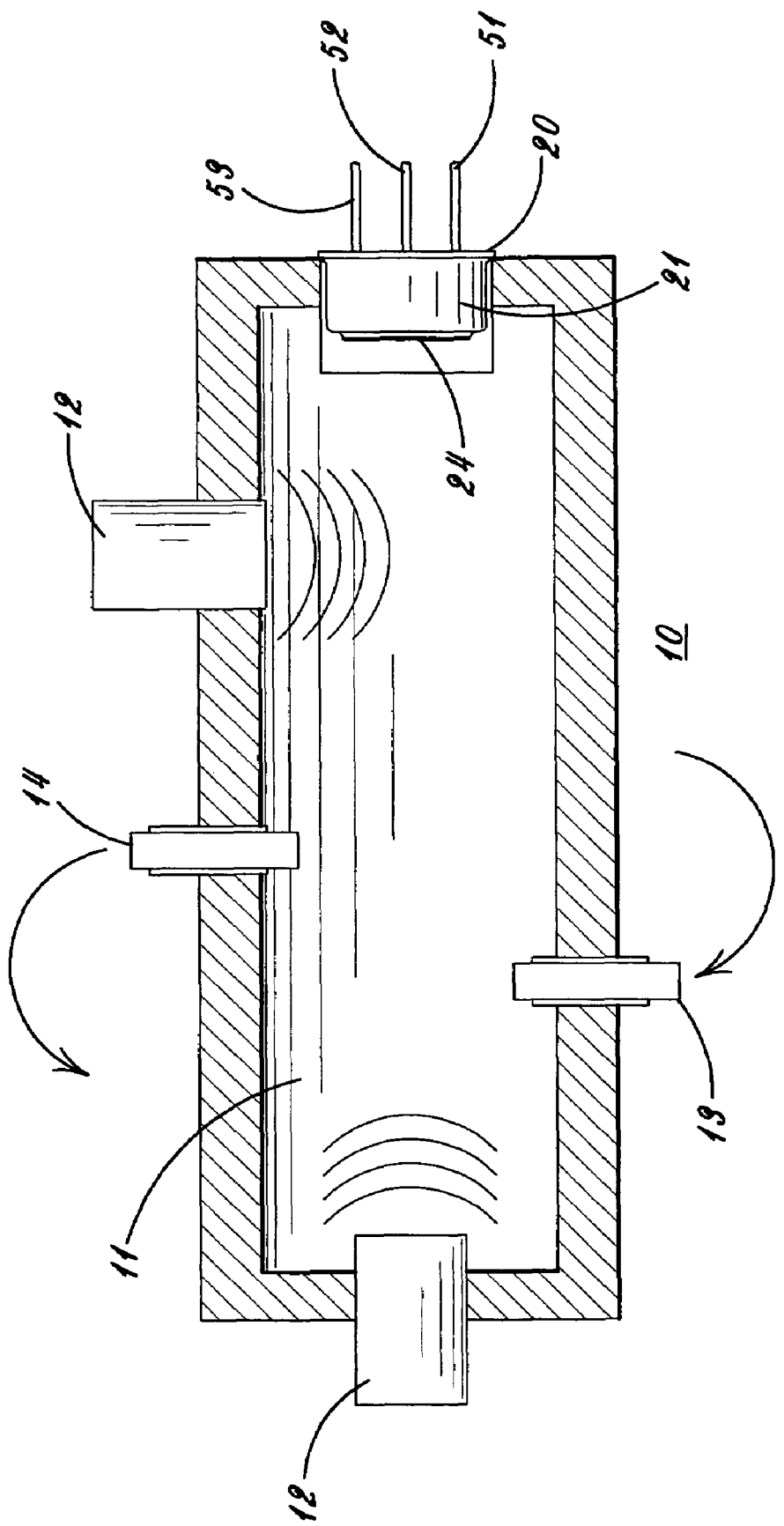
FIG. 1 is a plan view of the gas sensor apparatus of the invention.
Figure 2:
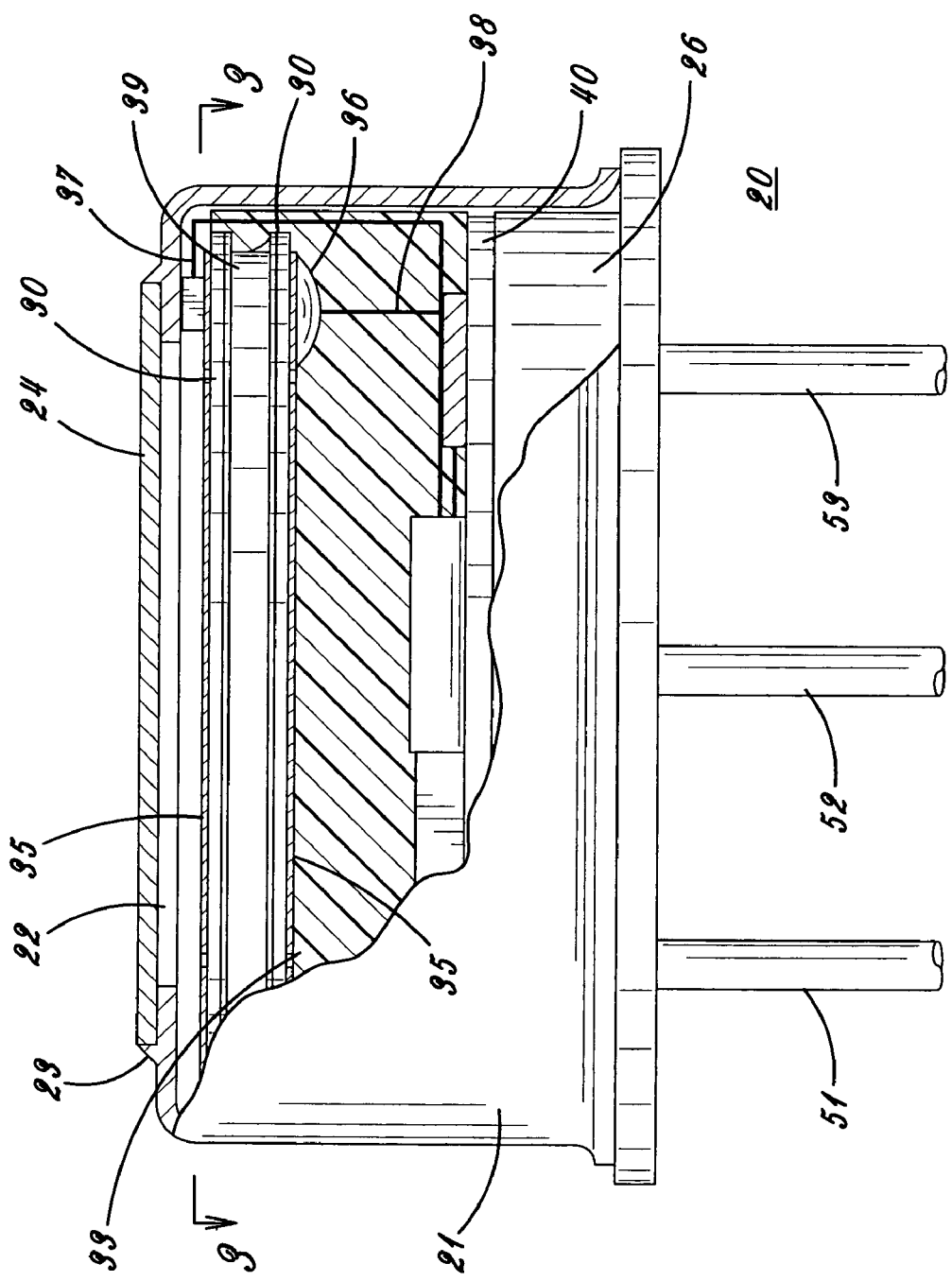
FIG. 2 is a side elevation view in partial section of a preferred embodiment of a housing assembly of the apparatus of the invention.
Figure 3:
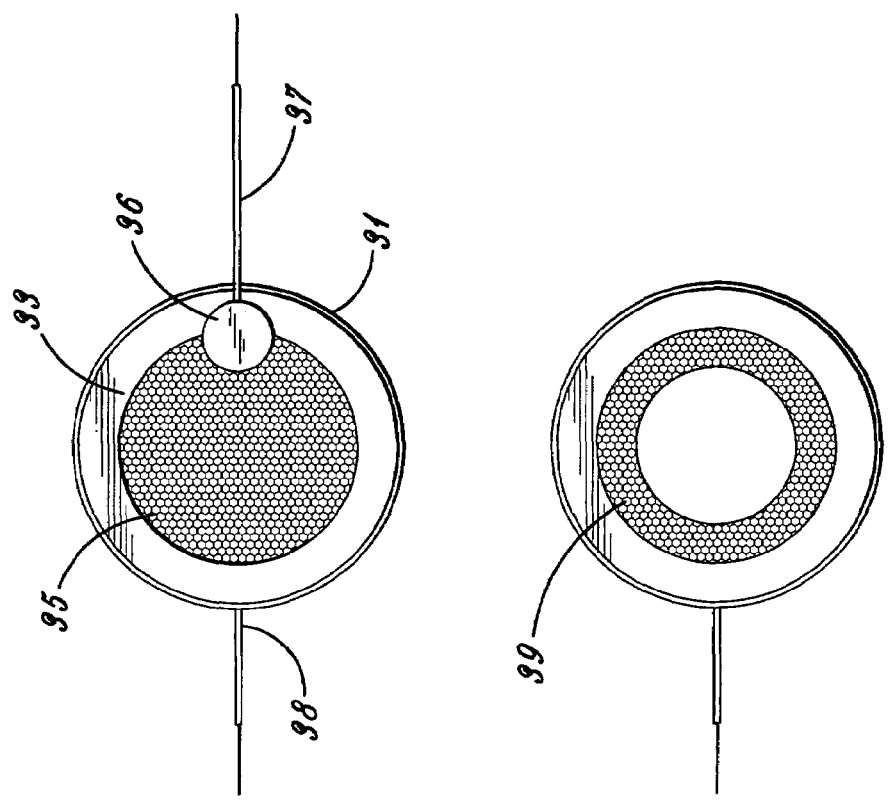
FIG. 3 is an exploded perspective view of the sensor element of the apparatus taken approximately on the line 3-3 of FIG. 2. A plan view and bottom view of the sensor element assembly.
Figure 3:
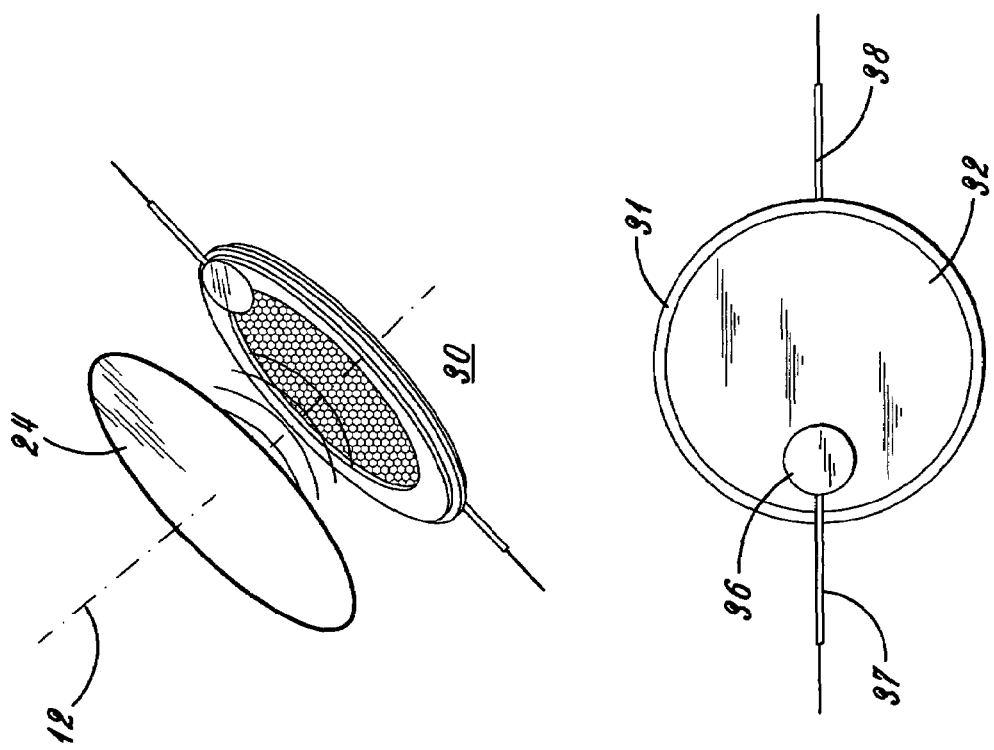
Figure 3A:
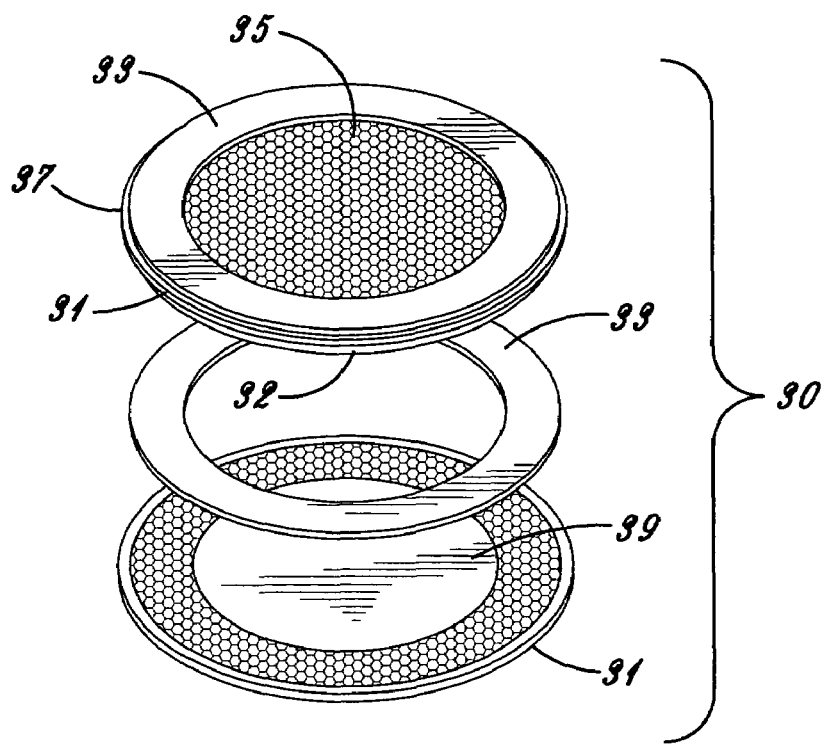
FIG. 3A is an exploded perspective view of a second sensor element of the apparatus shown in position when utilized for temperature and piezo effect compensation.
Figure 4:
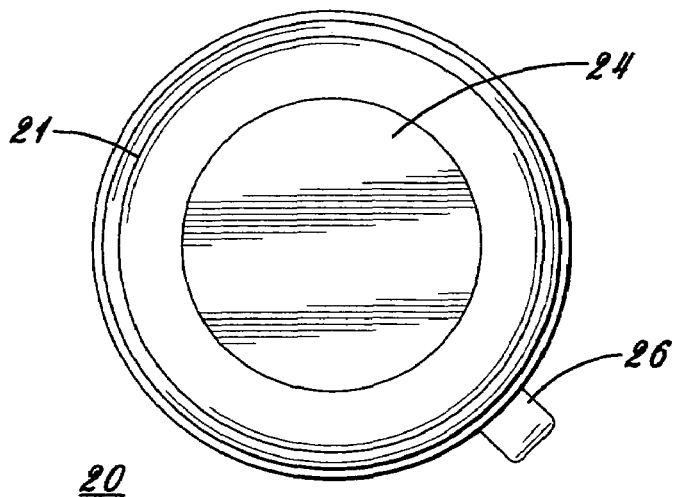
FIG. 4 is a top plan view of the housing assembly of FIG. 2.
Figure 5:
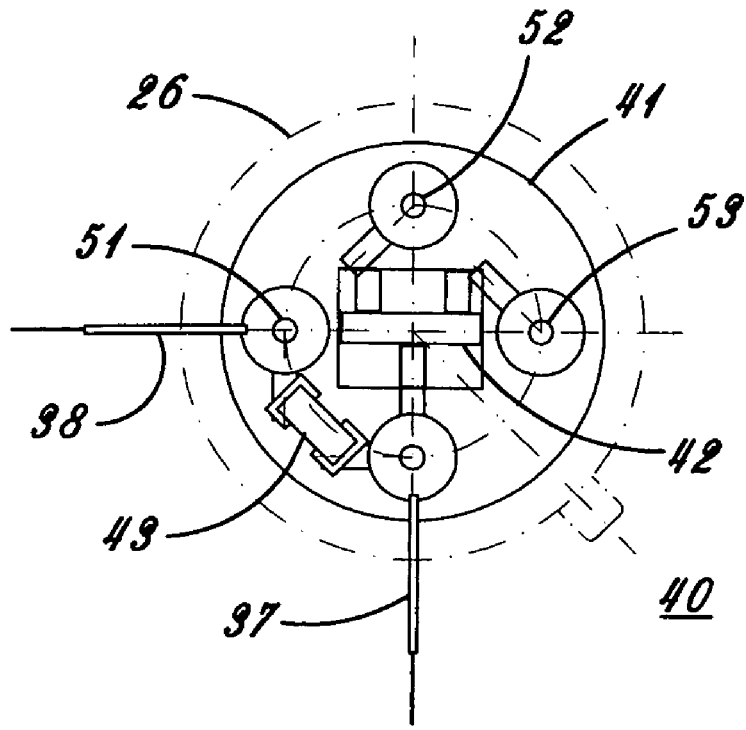
FIG. 5 is a top plan view of one embodiment of sensor element of the invention, and the sensor element assembly and printed circuit board.

Preferring now more particularly to the drawings and FIGS. 1-5 thereof the gas detector apparatus 10 is therein illustrated. The apparatus includes a chamber 11, with a gas inlet 13 and gas outlet 14. A multispectral infrared radiation (IR) source illuminator 12, is shown at the extreme end of chamber 11 and IR baseline reference illuminator 12 at the top of chamber 11, of well known type, and available from Gilway Technical Lamp, Woburn, Mass., emitting broadband IR radiation, including the wavelength absorbed by the selected gas. The IR source 12 supplies radiation, which is directed into chamber 11 towards a sensor assembly element 30, in a sensor assembly 20 to be described. A sensor assembly housing 21 is provided, preferably of metal, of cylindrical configuration, with an opening 22 at the top 23, and with an optical band pass infrared filter 24 placed in the opening 22, transmitting only radiation of the wavelength absorbed by the selected gas. The housing 21 is open at the bottom 25, and engaged with a can base 26. The sensor assembly 20, contains the sensor element assembly 30, which includes a conductive brass washer 33, bonded with an Ag based conductive adhesive or indium 34, a proprietarily enhanced layer of vacuum deposited Au 35, a layer of textured Quantum Ferroelectric (QFE) copolymer 31, to be described, an underside layer of vacuum deposited Al 32, and a lead 38, connected to the Al layer 32, by the conductive adhesive 36. One alternate embodiment will include an additional QFE sensor element assembly 30, stacked as shown in FIG. 3A, shielded from incoming IR radiation, utilizing the subtracted residual signal for temperature and piezo compensation. Between the sensor element assembly(ies) 30 and the PC board 41, a layer of potting 40 of well known type is provided. The lead 37 is connected to an amplifier circuit 42, an element of the signal conditioning assembly 40, consisting of a PC board 41, a capacitance/resistance voltage conversion element 43 and an amplifier circuit 42. The can base 26 has three pins 51, 52 and 53 connected to the PC board 41, and extending therefrom which are connected to commercial NDIR gas sensing devices of well known type available from Texas Instrument, E2V, MSA and others.

Figure 6:
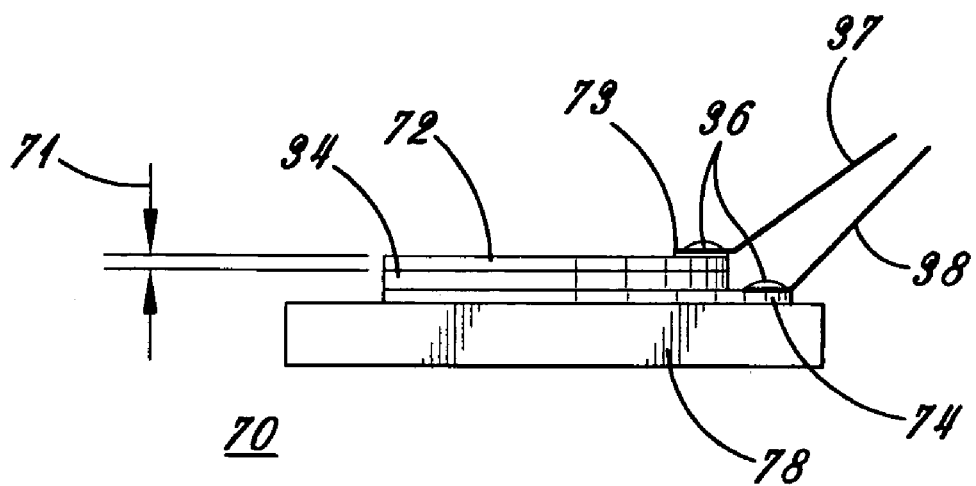
FIG. 6 is a sectional view of another embodiment of the sensor element of the invention.

Referring now to FIG. 6, a second alternate embodiment of QFE sensor element assembly 70 is therein illustrated. The assembly 70, includes a thin film layer of QFE copolymer 71, an Au absorber vacuum deposited coating 72, and a gold collector pad 73 on top of the Au absorber coating 72, bonded with a layer of Ag conductive adhesive 34, or indium and with a lead 37, connected thereto with conductive adhesive 34. The copolymer film 71, has a bottom layer of Ag adhesive 34 in contact therewith, which is in contact with (capacitance coupled to) an Ag vacuum deposited surface conductor on a metallic substrate 73, and with a lead 38, connected thereto. The conductive substrate 74, is supported by an alumia ceramic substrate 75.

The Quantum Ferroelectric Copolymers used in the sensor element assembly 28 and 75, are responsive to the infrared radiation provided by the IR source 14, which is affected by the gas in chamber 11, dependent upon the IR absorption bands of the gases to be detected. The Quantum Ferroelectric Copolymers of the invention are not affected by the presence of moisture. Laboratory tests have shown performance to be unaffected after being subjected to direct wetting after curing, and after prolonged submersion in water. The stability of photoelectric response and speed of responsivity in the Pyroelectric mode exceeds the performance of TriGlycine Sulfide, both TGS and DTGS. The Quantum Ferroelectric Copolymers are polar dielectric materials in which an increase in temperature (dT), due to absorbed thermal energy, causes a change in the material's electrical polarization (dp). This results in a measurable current ($I_{py}$) flowing out of the electrodes on the output surface of the Pyroelectric mode material. It can be shown that: $I_{py} = A\, dp/dT$ where A is the surface absorption area.

The Pyroelectric charge coefficient (p) of a material is given by: $p = dp/dT$ Other parameters commonly used to describe and evaluate thermally sensitive materials for use as infrared detectors are, Voltage Responsivity and Current Responsivity. In the case of Pyroelectric devices, Current Responsivity (R) is more significant. This parameter is defined as: $R = \rho/dC^1$ Where $\rho$ is the density, d is the thickness and $C^1$ is the specific heat of the Pyroelectric material. Other evaluation parameters include the Detectivity (D*) [D–Star], which is defined as: $D^* = KR/V_T + V_A + V_J$ Where k is a constant and $V_T$, $V_A$ and $V_J$ are the thermal, amplifier and Johnson noise voltages, and Noise Equivalent Power (NEP) which is proportional to the reciprocal of D*.

QFE copolymers have a Pyroelectric response characterization, which is electric polarization produced by infrared energy absorption. Upon exposure of QFE to a broad band of electromagnetic radiation (thermal energy included), the electric dipoles in the embodiment of the QFE material are forced to shift from equilibrium orientations, causing the net charge distribution to change within the material resulting in a measurable photoelectric voltage and current response. Irradiation by an external energy source, along with treatment of the QFE with wavelength specific, metallic evaporated, and/or sputtered coatings, disturbs the coatings, and disturbs the polarization, accompanied by an ejection of electrons from the output surface, yielding an initial Pyroelectric current response followed by a distinct photo current response.

Peak sensitivity of the QFE detector to selected wavebands in the infrared near and mid range is achieved by element metallization of the input and output surfaces of the detector. The QFE material is sensitive to radiation from x-ray, through ultra violet, through visible, through near, medium and thermal infrared. The specific vacuum deposited and/or sputtered metallic coatings are chosen on the basis of relative work function and texture, both playing a significant role in optimizing and maximizing the photoelectric response.

The copolymers used for gas detection and particularly Co and $Co_2$ gases were pyroelectric, and specifically, copolymers having the following compositions (i.e. ratios of difluoro: trifluorethylene): a 50/50 mole % poly(vinylidene difluoride-trifluooroethylene) or P(VDF/TrFE), a 65/35 mole % poly (vinylidene difluoride-trifluoroethylene) and a 72/28 mole % poly(vinylidene difluoride-trifluoroethylene) have been used for gas sensing applications. In addition to these three copolymer solutions, these pure copolymers were mixed with other copolymer solutions in an attempt to form even more responsive material. These solutions included a 50:50 mixture of 50/50 mole % poly(vinylidene difluoride-trifluoroethylene) with a 72/28 mole % poly(vinylidene difluoride-trifluoroethylene), a 50:50 mixture of 50/50 mole % poly(vinylidene difluoride-trifluoroethylene) with a 65/35 mole % poly(vinylidene difluoride-trifluoroethylene) and a 50:50 mixture of 65/35 mole % poly(vinylidene difluoride-trifluoroethylene) with a 72/28 mole % poly(vinylidene difluoride-trifluoroethylene). These compositions were found to produce acceptable results when used in the sensor element assemblies as described above. It was also noted that copolymer solutions that contained all three copolymers in equal amounts were also tested and produced acceptable detection results.

It will thus be seen that apparatus and copolymers have been described with which the objects of the invention are achieved.

We claim:

1. A gas sensor apparatus for sensing the presence of selected or target gasses in combination with multi-spectral sources of infrared radiation which comprises, a cylindrical housing or can open at both ends, an infrared filter closing off one end facing said radiation sources, a can base closing off the other end of said can, sensor element means in said housing adjacent said filter, including, a first brass washer at the top of said assembly means, a first layer of electrically conductive adhesive in contact with and under said washer, a first layer of Quantum Ferroelectric Copolymer under said adhesive responsive to infrared radiation from said infrared radiation source, a first layer of vacuum deposited Au coating on said Quantum Ferroelectric Copolymer in contact with and under said adhesive, a first layer of aluminum in contact with and under said first layer of copolymer, a first lead connected to said aluminum layer, and to amplifier circuit means connected to said first lead, whereby, upon bombardment of said first copolymer layer with infrared radiation from said source, said copolymer provides a measurable charge of photovoltaic and current output which signals the presence of a target or selected gas by its characteristic infrared radiation absorption band.

2. Apparatus as defined in claim 1 in which a second layer of electrically conductive adhesive is provided in contact with said first layer of aluminum, a second brass ring is provided in contact with said second layer of adhesive, a second layer of Au coated Quantum Ferroelectric copolymer is provided in contact with said second brass ring, a second vacuum deposited layer of aluminum is provided in contact with said second copolymer layer, a second lead is provided in contact with and extending from said second layer of aluminum to provide a subtracted residual signal for temperature and piezo compensation.

3. Apparatus as defined in claim 1 or 2 in which said Quantum Ferroelectric copolymer is a 50/50 mole % poly (vinylidene difluoride trifluoroethylene).

4. Apparatus as defined in claim 1 or 2 in which said Quantum Ferroelectric Copolymer is a 65/35% mole poly (vinylidene difluoride-trifluorethylene).

5. Apparatus as defined in claim 1 or 2 in which said Quantum Ferroelectric Copolymer is a 72/28 mole % poly (vinylidene difluoride-trifluoroethylene).

6. Apparatus as defined in claim 1 or 2 in which said Quantum Ferroelectric Copolymer is a 50:50 mixture of 50/50 mole % poly(vinylidene difluoride-trifluoroethylene) with a 72/28 mole % poly(vinylidene difluoride-trifluoroethylene).

7. Apparatus as defined in claim 1 or 2 in which said Quantum Ferroelectric Copolymer is a 50:50 mixture of 50/50 mole % poly(vinylidene difluoride-trifluoroethylene) with a 65/35 mole % poly(vinylidene difluoride-trifluoroethylene).

8. Apparatus as defined in claim 1 or 2 in which said Quantum Ferroelectric Copolymer is a 50:50 mixture of 65/35 mole % poly(vinylidene difluoride-trifluoroethylene) with a 72/28 mole % poly(vinylidene difluoride-trifluoroethylene).

9. Apparatus as defined in claim 1 or 2 in which said Quantum Ferroelectric Copolymer is a 1/3 /1/3 /1/3 mixture of 50/50 mole % poly(vinylidene difluoride-trifluoroethylene) or P(VDF/TrFE), 65/35 mole % poly (vinylidene difluoride-trifluoroethylene) and 72/28 mole % poly (vinylidene difluoride-trifluoroethylene).

* * * * *